United States Patent
Bristow

(10) Patent No.: US 10,206,390 B2
(45) Date of Patent: Feb. 19, 2019

(54) HERBICIDAL SUSPENSION CONCENTRATE

(71) Applicant: ROTAM AGROCHEM INTERNATIONAL CO., LTD, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 12 days.

(21) Appl. No.: 14/359,148

(22) PCT Filed: Nov. 13, 2012

(86) PCT No.: PCT/CN2012/084529
§ 371 (c)(1),
(2) Date: May 19, 2014

(87) PCT Pub. No.: WO2013/071852
PCT Pub. Date: May 23, 2013

(65) Prior Publication Data
US 2014/0296071 A1 Oct. 2, 2014

(30) Foreign Application Priority Data

Nov. 17, 2011 (GB) .................................. 1119857.9

(51) Int. Cl.
| | | |
|---|---|---|
| *A01N 25/04* | (2006.01) | |
| *A01N 25/22* | (2006.01) | |
| *A01N 47/36* | (2006.01) | |
| *A01N 43/54* | (2006.01) | |

(52) U.S. Cl.
CPC ............. *A01N 25/04* (2013.01); *A01N 25/22* (2013.01); *A01N 43/54* (2013.01); *A01N 47/36* (2013.01)

(58) Field of Classification Search
CPC ................................ A01N 47/36; A01N 25/04
See application file for complete search history.

(56) References Cited

U.S. PATENT DOCUMENTS

| | | | |
|---|---|---|---|
| 6,669,949 B2 | 12/2003 | Kennedy et al. | |
| 2005/0244357 A1 | 11/2005 | Sieverding et al. | |
| 2010/0029587 A1* | 2/2010 | Bruckner ................. | C07F 7/21 |
| | | | 514/63 |
| 2012/0322656 A1* | 12/2012 | Yoshii et al. ................. | 504/103 |

FOREIGN PATENT DOCUMENTS

| | | | | |
|---|---|---|---|---|
| CH | 101420849 A | | 4/2009 | |
| EP | 232067 A2 | * | 8/1987 | |
| EP | 0 313 317 B1 | * | 4/1992 | ............. A01N 47/36 |
| EP | 554015 A1 | * | 8/1993 | |
| WO | WO 2008/155108 A2 | * | 12/2008 | |
| WO | WO 2011/108607 A1 | * | 9/2011 | |

OTHER PUBLICATIONS

T.K. James and A. Rahman, Effect of Adjuvants and Stage of Growth on the Efficacy of Three Sulfonylurea Herbicides to Grass Weeds, Proc. 47th N.Z. Plant Protection Conf., 1994, 11-16.*
International Search Report for PCT/CN2012/084529 dated Feb. 28, 2013.

* cited by examiner

*Primary Examiner* — John Pak
*Assistant Examiner* — Nathan W Schlientz
(74) *Attorney, Agent, or Firm* — Dickinson Wright PLLC

(57) ABSTRACT

A herbicidal suspension concentrate composition is provided, the composition comprising at least one pyridine sulfonamide active ingredient and a polyether-polysiloxane. The pyridine sulfonamide compound preferably has the general formula (I):

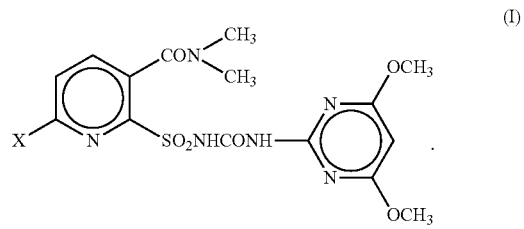

13 Claims, No Drawings

HERBICIDAL SUSPENSION CONCENTRATE

This application is a 371 of PCT/CN2012/084529, filed 13 Nov. 2012, which claims the benefit of Great Britain Patent Application 1119857.9, filed 17 Nov. 2011, the entire contents of each of which are incorporated herein by reference for all purposes.

BACKGROUND

Field

The present invention relates to a herbicidal suspension concentrate, more particularly to a herbicidal suspension concentrate comprising at least one sulfonamide compound and/or sulfonamide salt as the active ingredient.

Description of Related Art

When plant treatment products, in particular herbicides, are used, this may result in undesirable damage to the crop plants treated. While selective herbicides are intended to kill specific target plants and leave the desired crop relatively unharmed, a large number of selective herbicides are not one hundred percent effective in their selection, killing plant material intended for cultivation. Accordingly, the application of such herbicides on important crop plants may be substantially limited.

Occasionally, such herbicides cannot be used at all, or only at such low application rates that the desired, broad herbicidal activity against the harmful plants or unwanted plants cannot be guaranteed. In particular, herbicides of the pyridine sulfonamide class cannot be used to treat corn, rice or cereals with sufficient selectivity. Phytotoxic side-effects as a result of applying certain pyridine sulfonamides become apparent on the crop plants at various stages in the development of the plants, in particular, when the herbicides are applied post-emergence.

Accordingly, a herbicidal composition, in particular one comprising a pyridine sulfonamide as an active ingredient, capable of avoiding or reducing such phytotoxicity during the treatment of crop plants would be highly advantageous and is desirable.

Herbicidal compositions comprising pyridine sulfonamides as active ingredients are known in the art. Herbicidal active compounds from the group of the sulfonamide, such as, for example, N-[(4,6-dimethoxypyrimidin-2-yl)aminocarbonyl]-3-dimethylaminocarbonyl-2-pyridine sulfonamide, are predominantly formulated in the form of water-dispersible powders (WP) or water-dispersible granules (WG). One reason why solid formulations are preferred is that, in most cases, the pronounced sensitivity to hydrolysis of the active pyridine sulfonamide compounds. As pyridine sulfonamides are generally relatively soluble in water, the development of liquid water-based formulations is extremely difficult if the chemical stability of the sulfonamide is to be ensured. Thus, in the literature, storage-stable aqueous suspension concentrates (SC) and aqueous suspoemulsions (SE) comprising sulfonamides have been described only for a few special cases.

EP 0232067 discloses a herbicidal composition comprising a novel substituted pyridine sulfonamide compound and its salts as active ingredient and a method for preparing the same. In particular, EP 0232067 discloses that pyridine sulfonamide compounds exhibit a very high herbicidal effect and therefore may be applied to a wide range of weeds, including those which are highly resistant to other herbicides. EP 0232067 indicates that pyridine sulfonamide compounds and their salts are useful as herbicides for application on corn fields.

EP 0313317 discloses a suspended composition comprising at least one compound selected from the pyridine sulfonamide series of compounds and the salts thereof, a vegetable oil and a surfactant, mixed together at a predetermined ratio. EP 0313317 indicates that this composition improves the herbicidal effectiveness of the pyridine sulfonamide active ingredient without causing any unwanted crop injury. As a result, a much larger variety of weeds may be controlled. Furthermore, EP 0313317 suggests that the amount of the active pyridine sulfonamide ingredient to be used may be decreased. EP 0313317 indicates that inclusion of a vegetable oil within the admixture improves the weeding effect against a broad spectra of weeds, without causing any phytotoxicity in the crops to be protected, for example corn. However, the decomposition of herbicidal pyridine sulfonamide compounds within the oil-based suspension has been found to be a problem.

EP 05540158 discloses a method for suppressing or reducing the decomposition of certain herbicidally active compounds, including pyridinesulfonamides, so as to stabilize the formulations. EP 05540158 indicates this is achieved by adding urea to the herbicidal oil-based suspension formulation.

It has now been found, however, that oil-based suspension concentrates comprising pyridine sulfonamide compounds with urea as a stabilizer, as taught in EP 05540158, spread and disperse poorly in water. This has now been found to be due to the fact that the addition of urea induces a higher hydrophilic-lipophillic balance (HLB) value to the system, increasing water solubility.

It has also now been found that pyridine sulfonamide-containing oil-based suspension concentrates in combination with other suitable stabilizers also spread and disperse poorly in water.

Accordingly, it would be advantageous to provide a herbicidal formulation of one or more pyridine sulfonamide active ingredients, which exhibits a high degree of stability of the active ingredient, while reducing the phytotoxic effects of the formulation on the plants to be protected. It would be advantageous if such formulations maintained a broad spectrum of effectiveness against unwanted plants.

Surprisingly, it has now been found that modified polyether-polysiloxane is particularly suitable for solving the aforementioned difficulties of formulating oil-based suspension concentrates of pyridine sulfonamide active ingredients. In particular, polyether-polysiloxane has been found to significantly improve the stability of the pyridine sulfonamide compounds, while overcoming the problems of spreading and dispersibility in water.

SUMMARY

In a first aspect, the present invention provides a herbicidal suspension concentrate composition comprising at least one pyridine sulfonamide active ingredient and a polyether-polysiloxane, preferably a modified polyether-polysiloxane. Preferably the suspension concentrate further comprises a vegetable oil and/or mineral oil, a stabilizer, and one or more other suitable surfactants.

In one preferred embodiment, the present invention provides a herbicidal suspension concentrate composition comprising a sulfonamide compound represented by the general formula (I):

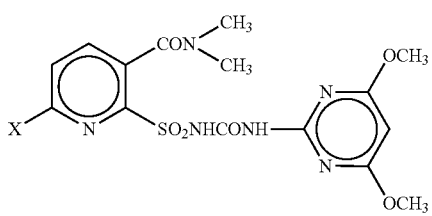

in which X is a hydrogen atom, a chlorine atom, a bromine atom, a methyl group, or a difluoromethyl group, or a salt thereof, as an active ingredient, and a polyether-polysiloxane. Preferably the suspension concentrate further comprises a vegetable oil and/or mineral oil, a stabilizer, a polyether-polysiloxane and one or more other suitable surfactants.

In a further aspect, the present invention provides the use of a polyether-siloxane, in particular a modified polyether-polysiloxane, in an oil-based suspension concentrate composition comprising at least one herbicidally active pyridine sulfonamide compound to improve the spreading and dispersibility of the formulation when diluted with water. The pyridine sulfonamide active ingredient is preferably a compound of general formula (I) described hereinbefore.

In a further aspect, the present invention provides an agrochemical composition comprising:

(a) 0.5%-20% of at least one herbicidally active pyridine sulfonamide compound, preferably a pyridine sulfonamide compound represented by the general formula (I) as described above;
(b) 50%-94.5% of a vegetable oil and/or mineral oil;
(c) 0.2%-10% of a stabilizer;
(d) 0.01%-10% of a polyether-polysiloxane.

The composition may further comprise from 2%-25% of other suitable surfactants.

In a still further aspect, the present invention provides a method of controlling plants at a locus, the method comprising applying to the locus a composition as hereinbefore described.

Still further, the present invention provides the use of a composition as hereinbefore described in the control of plants at a locus.

As noted above, it has been found that compositions according to the present invention exhibit a significantly improved speed of spreading on the surface of water when being diluted for application to plants at a locus, compared with the prior art compositions. In addition, the compositions of the present invention exhibit a significantly improved dispersibility in water when being diluted for application to plants at a locus, compared with the prior art compositions indicated above.

Accordingly, in a further aspect, the present invention provides the use of a polyether-polysiloxane to increase the spreading of a pyridine sulfonamide on the surface of water and/or to increase the dispersibility of the pyridine sulfonamide in water.

DETAILED DESCRIPTION OF SPECIFIC EMBODIMENTS

The compositions of the present invention are suspension concentrate formulations and comprise one or more herbicidally active pyridine sulfonamides as active ingredients. Suitable herbicidally active pyridine sulfonamides for use in the compositions of the present invention are known in the art and are commercially available.

Preferred pyridine sulfonamide compounds for use in the present invention are those having the general formula (I):

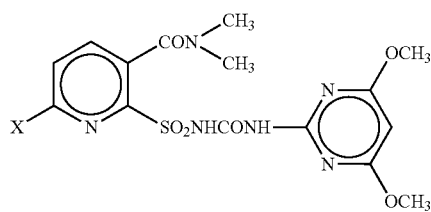

in which X is a hydrogen atom, a chlorine atom, a bromine atom, a methyl group, or a difluoromethyl group. The pyridine sulfonamide compound may be present in the composition as a salt.

Preferred sulfonamide compounds represented by the general formula (I) for use in the present invention include:
N-[(4,6-dimethoxypyrimidin-2-yl)aminocarbonyl]-3-dimethylaminocarbonyl-2-pyridinesulfonamide,
N-[(4,6-dimethoxypyrimidin-2-yl)aminocarbonyl]-6-chloro-3-dimethylaminocarbonyl-2-pyrinesulfonamide;
N-[(4,6-dimethoxypyrimidin-2-yl)aminocarbonyl]-6-bromo-3-dimethylaminocarbonyl-2-pyrinesulfonamide;
N-[(4,6-dimethoxypyrimidin-2-yl)aminocarbonyl]-3-dimethylaminocarbonyl -6-methyl-2-pyridinesulfonamide; and
N-[(4,6-dimethoxypyrimidin-2-yl)aminocarbonyl]-6-difluoromethyl-3-dimethylaminocarbonyl-2-pyridine-sulfonamide.

Suitable salts of the pyridine sulfonamide compounds for use in the present invention include those of alkali metals, such as sodium and potassium, those of alkali earth metals, such as magnesium and calcium, and those of amines, such as monomethylamine, dimethylamine and triethylamine. Examples of preferred salts are sodium and monomethylamine salts of
N-[(4,6-dimethoxypyrimidin-2-yl)aminocarbonyl]-3-dimethylaminocarbonyl-2-pyridinesulfonamide, and the dimethylamine salt of
N-[(4,6-dimethoxypyrimidin-2-yl)aminocarbonyl]-3-dimethylaminocarbonyl-6-methyl-2-pyridinesulfonamide.

The composition may comprise a single pyridine sulfonamide or salt thereof. Alternatively, the composition may comprise two or more pyridine sulfonamide compounds or salts thereof. The composition may comprise other active ingredients in combination with the pyridine sulfonamide, as required. Suitable other active ingredients for use in combination with the pyridine sulfonamide compounds are known in the art and commercially available.

Among the above-mentioned pyridine sulfonamide compounds, N-[(4,6-dimethoxypyrimidin-2-yl)aminocarbonyl]-3-dimethylaminocarbonyl-2-pyridinesulfonamide and its salts are particularly preferred compounds.

The pyridine sulfonamide compound may be present in the composition of the invention in any suitable amount to provide the desired herbicidal activity. Preferably, the pyridine sulfonamide active ingredient is present in an amount of from about 0.5% to 20% by weight, more preferably from 1.0% to 15% by weight, still more preferably from 1.5% to 10% by weight, more preferably from 2% to 6% by weight.

The suspension concentrate compositions of the present invention further comprise a polyether-polysiloxane. The polyether-polysiloxane is preferably a modified polyether-polysiloxane. The modified polyether-polysiloxanes are preferred, as they exhibit a better performance in terms of interface tension, critical micelle concentration (CMC), foam-forming ability, solubilizing capacity, and compatibility. Polyether-polysiloxane copolymers comprise a polyether chain linked to a polysiloxane chain. The modified polyether-polysiloxanes can be divided into the Si—O—C types and Si—C types, according to the different conjunction between the polyether chain segment and the polysiloxane chain segment.

One preferred range of polyether-polysilxanes are the polyether-polymethylsiloxane copolymers.

Suitable polyether-polysiloxanes for use in the present invention are known in the art and are commercially available. For example, modified polyether-polysiloxanes are available under the trade name Break-Thru 9902™, Break-Thru 9903™, Break-Thru 5503™, Break-Thru 9907™ and Break-Thru 9908™ (available from Degussa).

The polyether-polysiloxane may be present in the composition in any suitable amount, in particular in an amount sufficient to provide the required spreading and dispersibility of the concentrate formulation. Preferably, the polyether-polysiloxane is present in an amount of at least 0.01% by weight of the composition, more preferably at least 0.05%, still more preferably at least 0.1% by weight. Preferably, the polyether-polysiloxane is present in the composition in the range of from 0.01% to 10.0% by weight, more preferably from 0.05% to 7.5%, still more preferably from 0.1% to 5% by weight.

The composition of the present invention may comprise one or more vegetable oils and/or one or more mineral oils. Suitable vegetable and mineral oils for use in the present invention are known in the art and are commercially available. Examples of vegetable oils and mineral oil which can be used in the present invention include olive oil, kapok oil, castor oil, palm oil, camellia oil, coconut oil, sesame oil, corn oil, rice bran oil, peanut oil, cotton seed oil, soybean oil, rape seed oil, linseed oil, and tung oil, sunflower oil, safflower oil, and liquid paraffin. Vegetable oils are particularly preferred for use in the compositions of the present invention. Among these vegetable oils, corn oil and rapeseed oil are particularly preferred.

The vegetable oil and/or mineral oil may be present in any suitable amount. The amount of the vegetable oil and/or mineral oil in the composition of the invention is preferably from about 50% to 95% by weight, still more preferably from 60% to 90%, more preferably still from 75% to 90%. A vegetable and/or mineral oil content of at least 77% by weight is particularly preferred.

The composition of the present invention may comprise one or more suitable surfactants. Suitable surfactants are those effective to emulsify the above-mentioned vegetable and/or mineral oils in water. Suitable surfactants for use in the composition are known in the art and are commercially available. Examples of such surfactants include those of vegetable oil derivatives such as polyoxyethylene hydrogenated castor oil ether; nonionic surfactants, such as polyoxyethylene alkyl ethers, polyoxyethylene alkylaryl ethers, polyoxyethylene (propylene) fatty acid esters, sorbitan monooleate, ethoxylated castor oil and polyoxyethylene sorbitan monolaurate; and anionic surfactants, such as sodium alkylarylsulfonates, sodium dialkylsuccinate, sodium dialkylsulfosucciantes, polyoxyethylene alkylary ether sulfates, polyoxyethylene alkyl phosphates, polyoxyethylene alkylaryl phosphates, and sodium alkylnaphthalenesulfonates.

The composition preferably comprises a mixture of two or more surfactants, more particularly a mixture of a vegetable oil derivative, a nonionic surfactant and an anionic surfactant.

The one or more surfactants may be present in any suitable amount to provide the required dispersion and stability of the liquid concentrate formulation. In particular, the one or more surfactants may be present in an amount of at least 5% by weight, preferably at least 10%, more preferably at least 15% by weight. Preferably, the total surfactant concentration is in the range of from 5% to 25%. A surfactant concentration in the range of from 5% to 15% by weight has been found to be particularly suitable in many embodiments.

The composition preferably comprises a stabilizer. Suitable stabilizers are known in the art and are commercially available. Example of stabilizers which can be used in the composition of the present invention include a salt of a carboxylic or an inorganic acid, such as diammonium hydrogen phosphate, ammonium acetate, sodium acetate, potassium acetate, sodium thiocyanate; calcium carbonate, sodium triphosphate, urea, thiourea or derivatives thereof.

The amount of the stabilizer in the composition of the invention is generally from 0.2% to 10% by weight, more preferably from 1% to 8%, still more preferably from 2% to 6% by weight.

Methods and techniques for preparing the suspension concentrate of the present invention are known in the art and will be apparent to the person skilled in the art. An example of a suitable general method for preparing the suspension concentrate of the present invention is as follows:

One or more pyridine sulfonamide compounds is uniformly mixed with a vegetable oil and/or mineral oil and a surfactant. The resulting mixture is ground. Thereafter, the polyether-polysiloxane is added to the resulting ground mixture to obtain a suspension concentrate.

Alternatively, the active pyridine sulfonamide compound(s) are first finely divided, for example by grinding, and thereafter mixed with the vegetable oil and/or mineral oil, a surfactant and the polyether-polysiloxane to obtain a suspension concentrate.

If it is desired to increase the stability of the pyridine sulfonamide compound in suspension in the composition, one or more thixotropic materials, such as a bentonite-alkylamine complex and/or aerosol, may be added. If employed, the thixotropic material may be present in the composition in an amount of, for example, from 1% to 3% by weight, based on the total concentrate.

In use, the suspension concentrate composition of the present invention is typically diluted with water to provide a formulation for application to the plants to be treated. Techniques for diluting the composition with water are well known in the art. Similarly, techniques and equipment for applying the diluted formulation are well known in the art.

The rate at which the composition is applied to the plants or locus to be treated will vary according to parameters such as the nature and conditions of plants at the locus, the nature of plants to be controlled, and the properties of the active pyridine sulfonamide compound. In general, however, the composition is applied in an amount in the range of from 0.05 to 50 g/a, preferably from 0.1 to 25 g/a, and more preferably from 0.1 to 2.5 g/a, based on the amount of the active ingredient compound.

The composition and methods of the prevent invention will now be described, for illustrative purposes only, by way of the following specific examples.

Preparation of Suspension Concentrates

In the following compositions, Break-Thru 9902 and Break-Thru 9903 are both commercially available modified polyether-polysiloxanes. Sorpol 3742 is a mixture of polyoxyethylene styrylphenyl ether sulfate and dialkylsulfosuccinate. Sorpol 3005X is a mixture of polyoxyethylene di-styryl phenyl ether formaldehyde condensate and polyethylene tri-styryl phenyl ether.

FORMULATION EXAMPLE 1

A suspension concentrate formulation was prepared from the following components, with amounts indicated in terms of weight percent:

| | |
|---|---|
| (1) N-[(4,6-dimethoxypyrimidin-2-yl)aminocarbonyl]-3-dimethylaminocarbonyl-2-pyridinesulfonamide | 5% |
| (2) Corn oil | 90% |
| (3) Sorpol 3742 (ex. Toho Chemical) | 3.99% |
| (4) Bentonite-alkylamine complex | 0.8% |
| (5) Urea | 0.2% |
| (6) Break-Thru 9902 (Evonik) | 0.01% |

The above-mentioned components (1) to (5) were combined and mixed to form a uniform mixture. The resulting mixture was ground with a Dyno-Mill (manufactured by Willy A. Bachofen AG). Thereafter, component (6) was added the resulting mixture to obtain a suspension concentrate.

FORMULATION EXAMPLE 2

A suspension concentrate formulation was prepared from the following components, with amounts indicated in terms of weight percent:

| | |
|---|---|
| (1) N-[(4,6-dimethoxypyrimidin-2-yl)aminocarbonyl]-3-dimethylaminocarbonyl-2-pyridinesulfonamide | 10% |
| (2) Corn oil | 72.9% |
| (3) Sorpol 3005X (Toho Chemical) | 15% |
| (4) Bentonite-alkylamine complex | 1% |
| (5) urea | 1% |
| (6) Break-Thru 9903 (Evonik) | 0.1% |

The suspension concentrate was prepared following the method described in Example 1.

FORMULATION EXAMPLE 3

A suspension concentrate formulation was prepared from the following components, with amounts indicated in terms of weight percent:

| | |
|---|---|
| (1) N-[(4,6-dimethoxypyrimidin-2-yl)aminocarbonyl]-6-chloro-3-dimethylaminocarbonyl-2-pyrinesulfonamide | 17.5% |
| (2) Soybean oil | 50% |
| (3) Sorpol 3005X (Toho Chemical) | 25% |
| (4) Bentonite-alkylamine complex | 2% |
| (5) calcium carbonate | 5% |
| (6) Break-Thru 9902 (Evonik) | 0.5% |

The suspension concentrate composition was prepared using the method described in Example 1.

FORMULATION EXAMPLE 4

A suspension concentrate formulation was prepared from the following components, with amounts indicated in terms of weight percent:

| | |
|---|---|
| (1) N-[(4,6-dimethoxypyrimidin-2-yl)aminocarbonyl]-6-bromo-3-dimethylaminocarbonyl-2-pyrinesulfonamide | 20% |
| (2) Soybean oil | 62% |
| (3) Sorpol 3005X (Toho Chemical) | 5% |
| (4) Bentonite-alkylamine complex | 2% |
| (5) sodium acetate | 10% |
| (6) Break-Thru 9902 (Evonik) | 1% |

The suspension concentrate was prepared using the method described in Example 1.

FORMULATION EXAMPLE 5

A suspension concentrate formulation was prepared from the following components, with amounts indicated in terms of weight percent:

| | |
|---|---|
| (1) N-[(4,6-dimethoxypyrimidin-2-yl)aminocarbonyl]-3-dimethylaminocarbonyl-6-methyl-2-pyridinesulfonamide | 0.5% |
| (2) peanut oil | 74.5% |
| (3) Sorpol 3742 (Toho Chemical) | 13% |
| (4) Bentonite-alkylamine complex | 2% |
| (5) urea | 5% |
| (6) Break-Thru 9902 (Evonik) | 5% |

The suspension concentrate was prepared using the method described in Example 1.

FORMULATION EXAMPLE 6

A suspension concentrate formulation was prepared from the following components, with amounts indicated in terms of weight percent:

| | |
|---|---|
| (1) N-[(4,6-dimethoxypyrimidin-2-yl)aminocarbonyl]-6-difluoromethyl-3-dimethylaminocarbonyl-2-pyridine-sulfonamide | 6% |
| (2) peanut oil | 77% |
| (3) Sorpol 3742 (Toho Chemical) | 3% |
| (4) Bentonite-alkylamine complex | 2% |
| (5) urea | 2% |
| (6) Break-Thru 9902 (Evonik) | 10% |

The suspension concentrate composition was prepared using the method 15 described in Example 1.

FORMULATION EXAMPLE 7

A suspension concentrate formulation was prepared from the following components, with amounts indicated in terms of weight percent:

| | |
|---|---|
| (1) N-[(4,6-dimethoxypyrimidin-2-yl)aminocarbonyl]-3-dimethylaminocarbonyl-2-pyridinesulfonamide | 2% |
| (2) coconut oil | 94.5% |
| (3) Sorpol 3742 (Toho Chemical) | 1.5% |
| (4) Bentonite-alkylamine complex | 1% |
| (5) urea | 0.5% |
| (6) Break-Thru 9902 (Evonik) | 0.5% |

The suspension concentrate composition was prepared using the method described in Example 1.

Test of Spreading and Dispersibility Upon Dilution with Water

The compositions of Examples 1 to 6 were tested to determine the spreading speed on the surface of water and dispersibility in water using the following procedure.

A 1 ml sample of each composition was added to the surface of 250 ml of water in a cylinder. The results of adding each sample in this manner were observed. If the sample did not spread on the water surface and kept a fluid drop state on the water surface, it indicated that the spreading speed was slow. If the sample spread readily across the surface of the water, this indicated a quick spreading rate. Thereafter, each cylinder was gently shaken. If the sample did not readily disperse, it indicated that the dispersibility was bad. If the sample dispersed quickly and voluntarily, it indicated that the dispersibility of the sample in water was very good.

The performance of the composition of each of Example 1 to 6 was determined in this manner. Each composition was compared with a comparative composition prepared in an identical manner from the same components, but without the inclusion of a polyether-polysiloxane.

The results of the observations are set out in the following table.

| Example | spread speed on water surface | Dispersibility in water |
| --- | --- | --- |
| Example 1 | Quick | Very good |
| Comparison 1 | Slow | Bad |
| Example 2 | Quick | Very good |
| Comparison 2 | Slow | Bad |
| Example 3 | Quick | Very good |
| Comparison 3 | Slow | Bad |
| Example 4 | Quick | Very good |
| Comparison 4 | Slow | Bad |
| Example 5 | Quick | Very good |
| Comparison 5 | Slow | Bad |
| Example 6 | Quick | Very good |
| Comparison 6 | Slow | Bad |

The results set out in the Table show that the compositions of Examples 1 to 6 according to the present invention and comprising a polyether-polysiloxane exhibit a quick spreading speed on the surface of water and very good dispersibility in water, when the suspension concentrates are diluted. By comparison, the same compositions without a polyether-polysiloxane exhibited only a slow spreading speed on water and a poor dispersibility in water.

What is claimed is:

1. A herbicidal suspension concentrate composition comprising:
    0.5%-20% by weight of at least one pyridine sulfonamide compound selected from the group consisting of:
        N-[(4,6-dimethoxypyrimidin-2-yl)aminocarbonyl]-3-dimethylaminocarbonyl-2-pyridinesulfonamide;
        N-[(4,6-dimethoxypyrimidin-2-yl)aminocarbonyl]-6-chloro-3-dimethylaminocarbonyl-2-pyridinesulfonamide;
        N-[(4,6-dimethoxypyrimidin-2-yl)aminocarbonyl]-6-bromo-3-dimethylaminocarbonyl-2-pyridinesulfonamide;
        N-[(4,6-dimethoxypyrimidin-2-yl)aminocarbonyl]-3-dimethylaminocarbonyl-6-methyl-2-pyridinesulfonamide;
        N-[(4,6-dimethoxypyrimidin-2-yl)aminocarbonyl]-6-difluoromethyl-3-dimethylaminocarbonyl-2-pyridinesulfonamide, and
    alkali metal, alkaline earth metal, or amine salts thereof;
    0.01%-10% by weight of polyether-polysiloxane;
    50%-94.5% by weight of a vegetable oil;
    one or more surfactants; and
    0.2%-10% by weight of a stabilizer; and
    wherein the suspension concentrate contains no mineral oil.

2. The composition according to claim 1, wherein the pyridine sulfonamide compound is selected from:
    N-[(4,6-dimethoxypyrimidin-2-yl)aminocarbonyl]-3-dimethylaminocarbonyl-2-pyridinesulfonamide;
    N-[(4,6-dimethoxypyrimidin-2-yl)aminocarbonyl]-6-chloro-3-dimethylaminocarbonyl-2-pyridinesulfonamide;
    N-[(4,6-dimethoxypyrimidin-2-yl)aminocarbonyl]-6-bromo-3-dimethylaminocarbonyl-2-pyridinesulfonamide;
    N-[(4,6-dimethoxypyrimidin-2-yl)aminocarbonyl]-3-dimethylaminocarbonyl-6-methyl-2-pyridinesulfonamide; and
    N-[(4,6-dimethoxypyrimidin-2-yl)aminocarbonyl]-6-difluoromethyl-3-dimethylaminocarbonyl-2-pyridinesulfonamide.

3. The composition according to claim 1, wherein the pyridine sulfonamide compound is a sodium, potassium, magnesium, calcium, monomethylamine, dimethylamine, or trimethylamine salt.

4. The composition according to claim 3, wherein the pyridine sulfonamide compound is the sodium or monomethylamine salt of N-[(4,6-dimethoxypyrimidin-2-yl)aminocarbonyl]-3-dimethylaminocarbonyl-2-pyridinesulfonamide; or the dimethylamine salt of N-[(4,6-dimethoxypyrimidin-2-yl)aminocarbonyl]-3-dimethylaminocarbonyl-6-methyl-2-pyridinesulfonamide.

5. The composition according to claim 1, wherein the pyridine sulfonamide compound is N-[(4,6-dimethoxypyrimidin-2-yl)aminocarbonyl-3-dimethylaminocarbonyl-2-pyridinesulfonamide or a alkali metal, alkali earth metal, or amine salt thereof.

6. The composition according to claim 1, comprising two or more pyridine sulfonamide compounds.

7. The composition according to claim 1, wherein the pyridine sulfonamide compound is present in an amount of from 2% to 6% by weight.

8. The composition according to claim 1, wherein the oil content is from 50 to 90% by weight.

9. The composition according to claim 1, wherein the composition comprises a nonionic surfactant and an anionic surfactant.

10. The composition according to claim 1, wherein the surfactant is present in an amount of at least 5% by weight.

11. The composition according to claim 1, wherein the stabilizer is present in an amount of from 0.2 to 10% by weight.

12. A method of controlling plants at a locus, the method comprising applying to the locus a composition according to claim 1.

13. A method of increasing the spreading of a pyridine sulfonamide on the surface of water or increasing the dispersibility of the pyridine sulfonamide in water comprising incorporating the pyridine sulfonamide into a composition wherein the resulting composition comprises:
    0.5%-20% by weight of pyridine sulfonamide;
    0.01%-10% by weight of polyether-polysiloxane;
    50%-94.5% by weight of a vegetable oil;
    one or more surfactants;
    0.2%-10% by weight of a stabilizer; and
    no mineral oils.

* * * * *